US009848859B2

(12) United States Patent
White

(10) Patent No.: US 9,848,859 B2
(45) Date of Patent: Dec. 26, 2017

(54) TISSUE PUNCTURE CLOSURE DEVICE WITH LIMITED FORCE AUTO COMPACTION

(75) Inventor: Troy T. White, Maple Grove, MN (US)

(73) Assignee: TERUMO PUERTO RICO, L.L.C., Caguas, PR (US)

( * ) Notice: Subject to any disclaimer, the term of this patent is extended or adjusted under 35 U.S.C. 154(b) by 1102 days.

(21) Appl. No.: 14/112,019

(22) PCT Filed: Apr. 18, 2012

(86) PCT No.: PCT/US2012/034015
§ 371 (c)(1),
(2), (4) Date: Oct. 24, 2013

(87) PCT Pub. No.: WO2012/145356
PCT Pub. Date: Oct. 26, 2012

(65) Prior Publication Data
US 2014/0039547 A1 Feb. 6, 2014

Related U.S. Application Data

(60) Provisional application No. 61/477,541, filed on Apr. 20, 2011.

(51) Int. Cl.
*A61B 17/04* (2006.01)
*A61B 17/00* (2006.01)
*A61B 90/00* (2016.01)

(52) U.S. Cl.
CPC *A61B 17/0057* (2013.01); *A61B 2017/00654* (2013.01); *A61B 2017/00659* (2013.01);
(Continued)

(58) Field of Classification Search
CPC ........ A61B 17/0057; A61B 2090/0811; A61B 2017/0406; A61B 2017/00654;
(Continued)

(56) References Cited

U.S. PATENT DOCUMENTS 5,324,268 A * 6/1994 Yoon .................. A61B 17/3496
604/158
5,571,134 A * 11/1996 Yoon .................. A61B 10/0233
604/164.11
(Continued)

FOREIGN PATENT DOCUMENTS

| EP | 2064999 A2 | 6/2009 |
|---|---|---|
| WO | 2010129042 A1 | 11/2010 |
| WO | 2011100547 A2 | 8/2011 |

OTHER PUBLICATIONS

PCT International Search Report for PCT International Patent Application No. PCT/US2012/034015, dated Jul. 11, 2012.
(Continued)

*Primary Examiner* — Diane Yabut
*Assistant Examiner* — Erich Herbermann
(74) *Attorney, Agent, or Firm* — Buchanan Ingersoll & Rooney PC

(57) ABSTRACT

A closure device (200) includes a filament (204), an anchor (208), a sealing pad (210), and an automatic driving mechanism. The anchor is configured to be inserted through the tissue wall puncture and is attached to the filament at the second end of the closure device. The sealing pad is slidingly attached to the filament at the second end of the closure device. The automatic driving mechanism includes a compaction member (212), at least one slide member (230, 232) at the first end of the closure device, and a biasing member (234). The biasing member is carried by the at least one slide member and operable to distally advance the compaction member for automatically compacting the sealing pad toward the anchor upon withdrawal of the closure device from the internal tissue wall puncture.

17 Claims, 12 Drawing Sheets

(52) U.S. Cl.
CPC ............... *A61B 2017/00898* (2013.01); *A61B 2017/0406* (2013.01); *A61B 2090/0811* (2016.02)

(58) Field of Classification Search
CPC ........... A61B 2017/00659; A61B 2017/00898; A61B 2017/00588; A61B 2017/00628; A61B 2017/00619; A61B 2017/0061; A61B 2017/00637; A61M 25/0136; A61M 25/0631
USPC ................................................. 606/213, 185
See application file for complete search history.

(56) References Cited

U.S. PATENT DOCUMENTS

| | | | |
|---|---|---|---|
| 6,045,569 A | | 4/2000 | Kensey et al. |
| 6,090,130 A | | 7/2000 | Nash et al. |
| 2005/0125031 A1 | | 6/2005 | Pipenhagen et al. |
| 2008/0065121 A1 | | 3/2008 | Kawaura et al. |
| 2011/0196388 A1* | | 8/2011 | Thielen .............. A61B 17/0057 606/144 |

OTHER PUBLICATIONS

Office Action (Communication pursuant to Article 94(3) EPC) dated Mar. 24, 2017 by the European Patent Office in corresponding European Patent Application No. 12 720 321.4-1664. (5 pages).

* cited by examiner

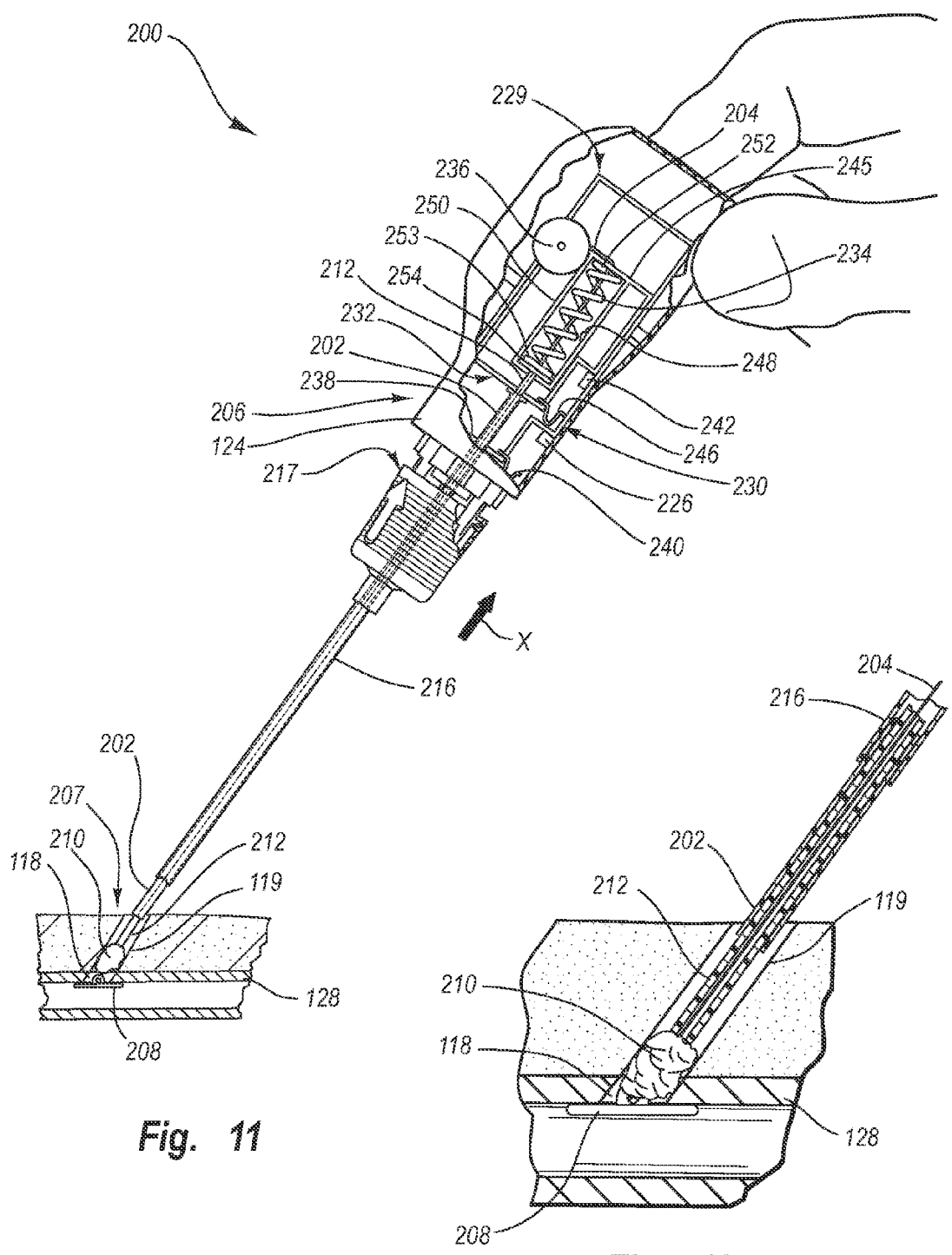

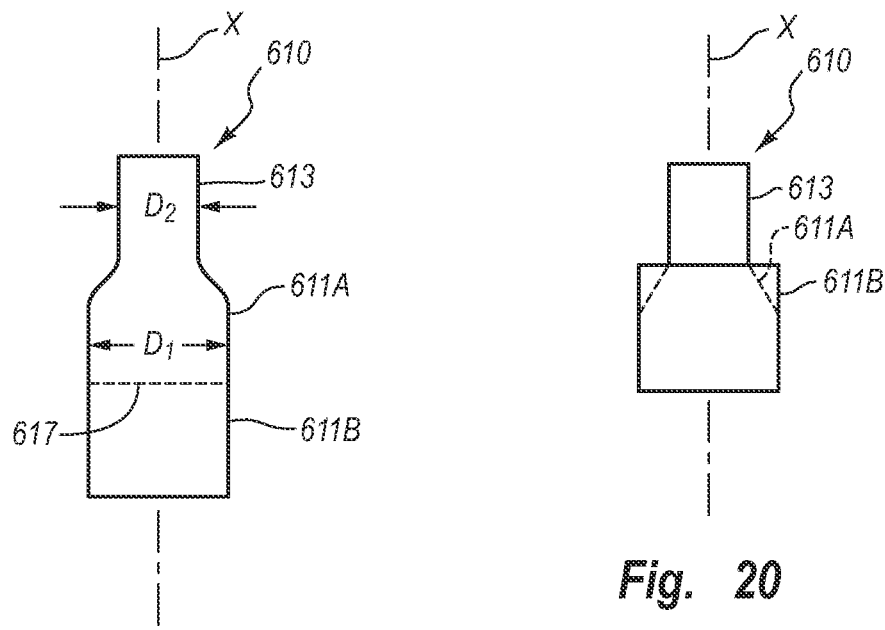
Fig. 19
Fig. 20
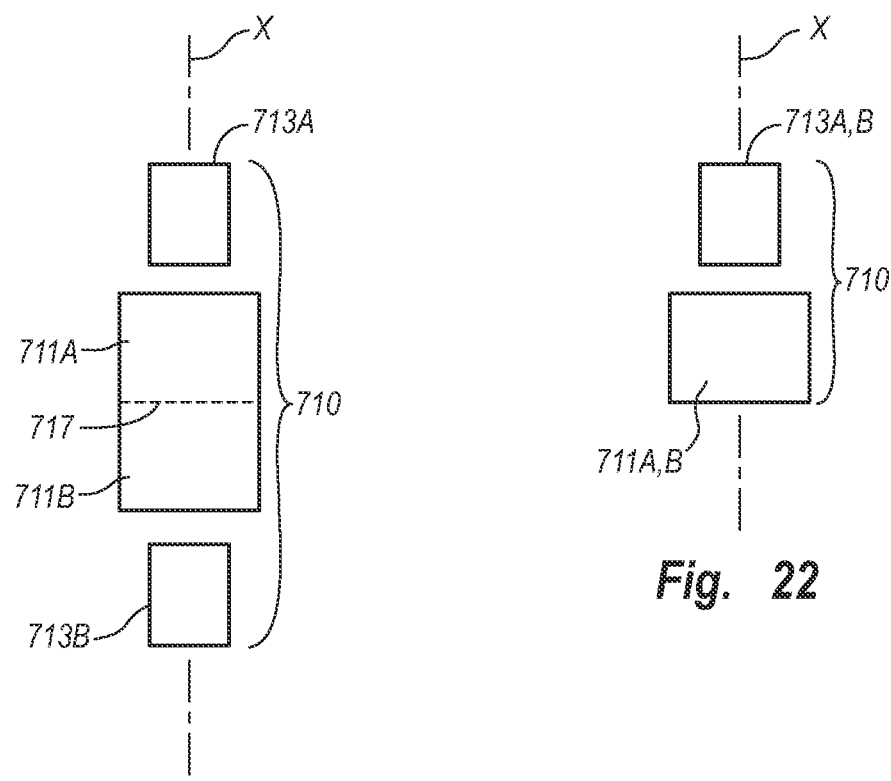
Fig. 21
Fig. 22

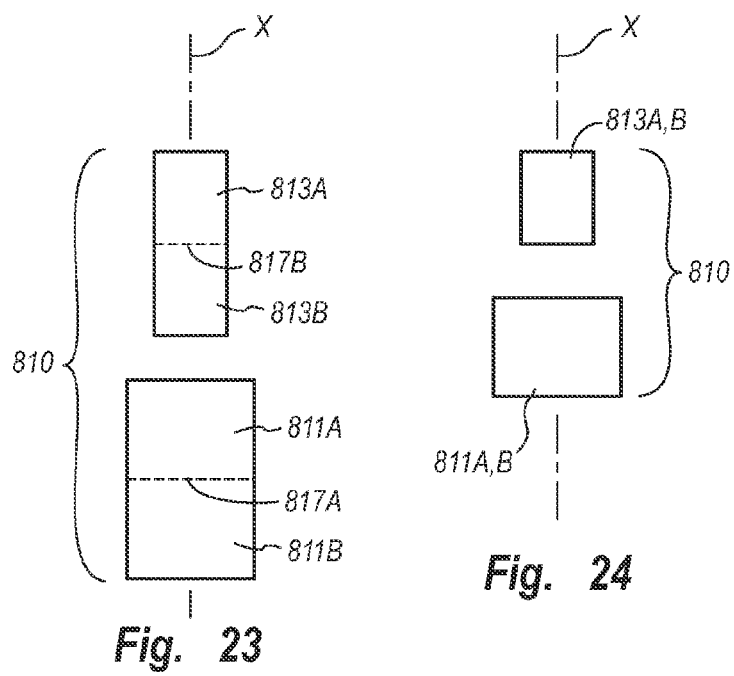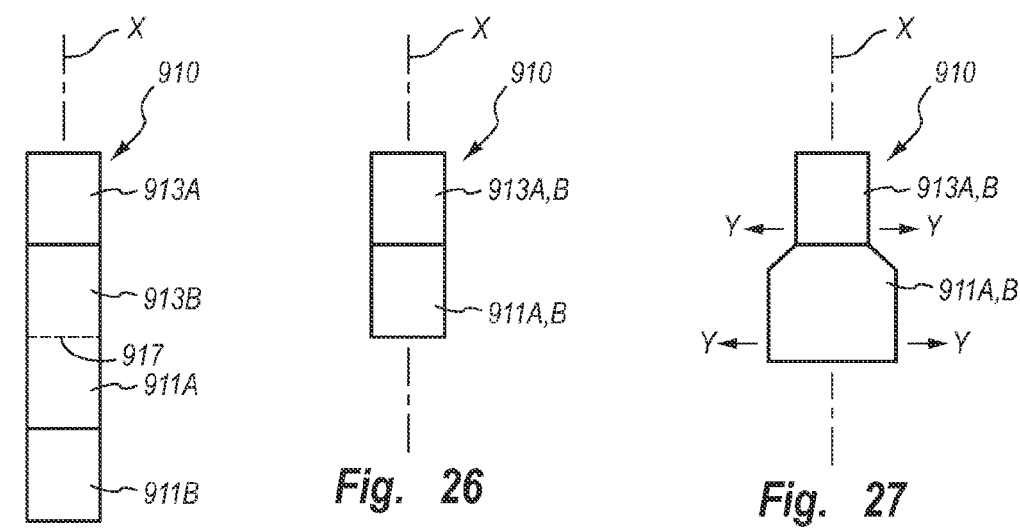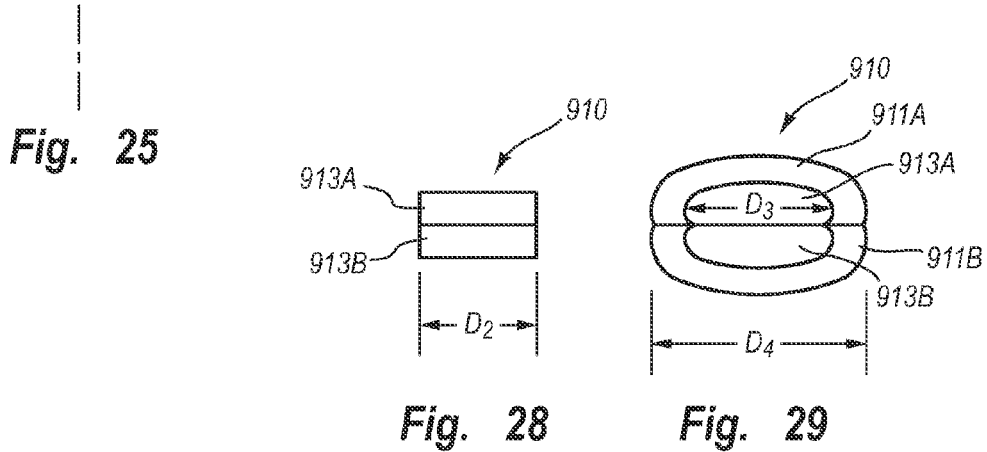

TISSUE PUNCTURE CLOSURE DEVICE WITH LIMITED FORCE AUTO COMPACTION

RELATED APPLICATION

This claims the benefit of U.S. Provisional Application No. 61/477,541, filed 20 Apr. 2011, which is hereby incorporated by reference herein its entirety.

TECHNICAL FIELD

The present disclosure relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties by this reference.

Typical closure devices such as the ones described in the above-mentioned patents place a sealing pad at the tissue puncture site. Deployment of the sealing pad may include manually ejecting the sealing pad from within a device sheath and compacting the sealing pad against an outer surface of the tissue puncture using a compaction member. The compacting procedure may begin after the device sheath (within which the compaction member may be located) has been removed. Under certain conditions, removal of the sheath prior to compacting the sealing pad may cause the sealing pad itself to be displaced proximally from the tissue puncture, hindering subsequent placement of the sealing pad, and resulting in only a partial seal and associated late bleeding from the tissue puncture. Accordingly, there is a need for improving the mechanism for deployment of the sealing pad at the site of a tissue puncture.

SUMMARY

One aspect of the present disclosure relates to a tissue puncture closure device for partial insertion into and sealing of an internal tissue wall puncture. The closure device includes a filament, an anchor, a sealing pad, and an automatic driving mechanism. The filament extends from a first end of the closure device to a second end of the closure device. The anchor is configured to be inserted through the tissue wall puncture and is attached to the filament at the second end of the closure device. The sealing pad is slidingly attached to the filament at the second end of the closure device. The automatic driving mechanism includes a compaction member, at least one slide member at the first end of the closure device, and a biasing member. The biasing member is carried by the at least one slide member and operable to distally advance the compaction member for automatically compacting the sealing pad toward the anchor upon withdrawal of the closure device from the internal tissue wall puncture.

The closure device may further include a housing positioned at the first end of the closure device, wherein the at least one slide member includes a first slide positioned in and movable relative to the housing. The closure device may also include a second slide positioned in and movable relative to the housing, wherein the first slide is carried by and movable relative to the second slide. The automatic driving mechanism may further comprises a filament spool carried by the first slide and having a portion of the filament wound thereon. The biasing member may be arranged coaxially with the compaction member. The biasing member may be, for example, a compression, extension, constant force, or coil spring. The biasing member may be arranged parallel with a direction of movement of the compaction member toward the sealing pad.

The automatic driving mechanism further includes first, second and third automatic release members operable upon withdrawal of the closure device from the internal tissue wall puncture. The first automatic release member is operable to release the biasing member to advance the compaction member. The second release member is operable to release the first slide to move between first and second positions relative to the housing. The third automatic release member is operable to release the second slide to move between first and second positions relative to the housing. An amount of force applied upon withdrawal of the closure device required to activate any one of the automatic release members is typically no greater than about 1 lb. An amount of force applied by the biasing member to the compaction member to compact the sealing pad is typically no greater than about 1 lb.

Another aspect of the present disclosure is directed to a tissue puncture closure device for partial insertion into and sealing of a tissue puncture. The closure device includes an anchor, a sealing pad, a filament, a compaction member, a housing, a storage spool, a biasing member, and a first slide member. The anchor is configured for positioning on a distal side of the internal tissue wall. The sealing pad is configured for positioning on a proximal side of the internal tissue wall. The filament is connected at a distal end to the anchor and sealing pad for slidably cinching the anchor and sealing pad together about the tissue puncture. The sealing pad and compaction member are slidably disposed on the filament proximal to the anchor. The compaction member is disposed on the filament. The housing is arranged proximal of the anchor and sealing pad. The storage spool is positioned in the housing onto which a proximal end of the filament is wound. The biasing member is positioned in the housing and automatically activated to drive the compaction member along the filament distally towards the sealing pad upon withdrawal of the tissue puncture closure device. The first slide member is positioned in and movable relative to the housing, wherein at least the storage spool and biasing member are carried by the first slide member.

The biasing member may be aligned parallel with a direction of movement of the compaction member toward the sealing pad. The biasing member may be, for example, a compression, extension, constant force, or coil spring. The closure device may further include a second slide member positioned in and movable relative to the housing, wherein the second slide member carries the first slide member and is movable relative to the first slide member. The closure device may further include first and second automatic release members operable upon withdrawal of the closure device from the internal tissue wall puncture, the first automatic release member operable to release the biasing member to advance the compaction member, and the second release member operable to release the first slide member to move between first and second positions relative to the housing.

A further aspect of the present disclosure is directed to a method of sealing a tissue puncture in a vessel, wherein the tissue puncture is accessible through a percutaneous incision. The method includes providing a tissue puncture closure device including a filament, an anchor, a sealing pad, a housing, and an automatic driving mechanism. The automatic driving mechanism includes a compaction member, a first slide member, and a biasing member, wherein the first slide member carries the biasing member. The method may also include inserting the anchor through the tissue puncture and into the vessel, withdrawing the tissue puncture closure device a first distance while automatically moving the first slide member distally within the housing, withdrawing the tissue puncture closure device a second distance to dispose the sealing pad adjacent to the tissue puncture outside of the vessel, and automatically releasing the biasing member upon further withdrawal of the tissue puncture closure device to advance the compaction member distally to compact the sealing pad toward the anchor.

The method may also include providing an insertion sheath, and the tissue puncture closure device further includes a carrier tube, wherein inserting the insertion sheath into the vessel puncture, and inserting the anchor includes inserting through the insertion sheath and into the vessel. Withdrawing the tissue puncture closure device a second distance may include withdrawing the carrier tube proximally out of the percutaneous incision to expose the sealing pad in the percutaneous incision. Withdrawing the tissue puncture closure device a first distance may include withdrawing the insertion sheath proximally out of the percutaneous incision. The tissue puncture closure device may further include a second slide member positioned in the housing and carried by the first slide member, wherein withdrawing the tissue puncture closure device a second distance moves the second slide distally relative to the first slide.

Additional advantages and novel features of the invention will be set forth in the description which follows or may be learned by those skilled in the art through reading these materials or practicing the examples disclosed herein.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

FIG. 11 is a side view of the tissue closure device and insertion sheath of FIG. 5 shown engaged with an artery in a fourth position and compacting a sealing pad.

FIG. 12 is a detailed insert of FIG. 11.

FIG. 19 is a side view of an example sealing pad according to the present disclosure for use with the tissue closure device of FIG. 5.

FIG. 20 is an end view of the sealing pad of FIG. 19.

FIG. 21 is a side view of an example sealing pad according to the present disclosure for use with the tissue closure device of FIG. 5.

FIG. 22 is an end view of the sealing pad of FIG. 21.

FIG. 23 is a side view of an example sealing pad according to the present disclosure for use with the tissue closure device of FIG. 5.

FIG. 24 is an end view of the sealing pad of FIG. 23.

FIG. 25 is a side view of an example sealing pad according to the present disclosure for use with the tissue closure device of FIG. 5.

FIG. 26 is a side view of the sealing pad of FIG. 25 in a folded state.

FIG. 27 is a side view of the sealing pad of FIG. 25 in an swelled state.

FIG. 28 is an end view of the sealing pad of FIG. 26.

FIG. 29 is an end view of the sealing pad of FIG. 27.

Throughout the drawings, identical reference numbers designate similar, but not necessarily identical, elements.

DETAILED DESCRIPTION

Figure 1:
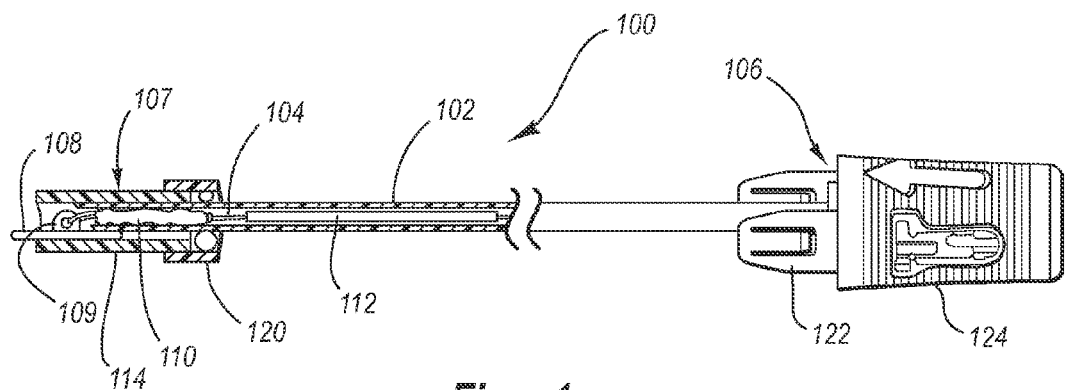
FIG. 1 is a side view of a tissue closure device according to the prior art.

As mentioned above, vascular procedures are conducted throughout the world and require access to an artery through a puncture. Most often, the artery is a femoral artery. To close the puncture following completion of the procedure, many times a closure device is used to sandwich the puncture between an anchor and a sealing pad. However, sometimes the sealing pad is difficult to eject from the sealing device and may not properly seat against an exterior situs of the arteriotomy. If the plug does not seat properly against the arteriotomy, there is a potential for elongated bleeding. The present disclosure describes methods and apparatus that facilitate sealing pad ejection and proper placement of the sealing pad. While the vascular instruments shown and described below include procedure sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims.

The present disclosure is directed to a tissue puncture closure device (generally referred to as a "closure device") that includes a sealing pad, a compaction member, and a biasing member that drives the compaction member to compact the sealing pad. The biasing member is typically a compression spring arranged parallel to the compaction member, wherein releasing the biasing member applies an axially directed force to the compaction member. In other arrangements, the biasing member includes an extension, constant force, or coil spring. Some rearrangement of parts may be useful depending on the type of biasing member used.

The closure device may also include a housing and first and second slide members. The first slide member carries the second slide member, and the second slide member carries the biasing member. The first and second slide members are movable relative to each other and to the housing. The first and second slide members and the biasing member are released to move relative to the housing at different times while withdrawing the closure device. In one example, the sequence of releasing the first and second slides and the biasing member first provide withdrawal of an insertion sheath (to which the closure device is connected) from the percutaneous incision, followed by withdrawal of a carrier tube of the closure device to expose the sealing pad in the percutaneous incision, followed by distally driving the compaction member to compact the sealing pad.

As used in this specification and the appended claims, the term "compact" or "compacting" is used broadly to mean any type of tamping (i.e., packing down by one or a succession of blows or taps or smooth, steady pressure, but not by excessive force), compacting, or compressing. "Engage" and "engabable" are also used broadly to mean interlock, mesh, or contact between two devices. Likewise "disengage" or "disengagable" means to remove or capable of being removed from interlock, mesh, or contact. A "spool" is a cylinder or other device on which something else is at least partially wound. A "tube" is an elongated device with a passageway. The passageway may be enclosed or open (e.g., a trough). A "lumen" refers to any open space or cavity in a bodily organ, especially in a blood vessel. "Slidingly mounted" means movable relative to an appropriate support. A "detent" is a catch or lever that locks, at least temporarily, the movement of one part of a mechanism. The words "including" and "having," as used in the specification, including the claims, have the same meaning as the word "comprising."

Referring now to the drawings, and in particular to FIGS. 1-4, a vascular puncture closure device 100 is shown according to the prior art. The vascular puncture closure device 100 includes a carrier tube 102 with a filament or filament 104 extending at least partially there through. The closure device 100 also includes a first or proximal end 106 and a second or distal end 107. External to the distal end 107 of the carrier tube 102 is an anchor 108. The anchor may be an elongated, generally stiff, low profile member including an eye 109 formed at the middle. The anchor 108 is typically made of a biologically resorbable polymer.

The filament 104 is threaded through the anchor 108 and back to a collagen pad 110. The collagen pad 110 may be comprised of, for example, randomly oriented fibrous material bound together by chemical means. The collagen pad 110 is slidingly attached to the filament 104 as the filament passes distally through the carrier tube 102. As the filament traverses the anchor 108 and reenters the carrier tube 102, the filament 104 is securely slip knotted proximal to the collagen pad 110 to facilitate cinching of the collagen pad 110 when the closure device 100 is properly placed and the anchor 108 deployed (see FIG. 4).

The carrier tube 102 typically includes a compaction member 112 disposed therein. The compaction member 112 is slidingly mounted on the filament 104 and may be used by an operator to compact the collagen pad 110 toward the anchor 108 at an appropriate time to seal a vascular puncture 118 within a percutaneous incision 119.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102 (see FIG. 1). The flush arrangement of the anchor 108 and carrier tube 102 allows the anchor 108 to be inserted into a procedure sheath such as insertion sheath 116 as shown in FIGS. 2-4, and eventually through an vascular puncture 118.

Figure 2:
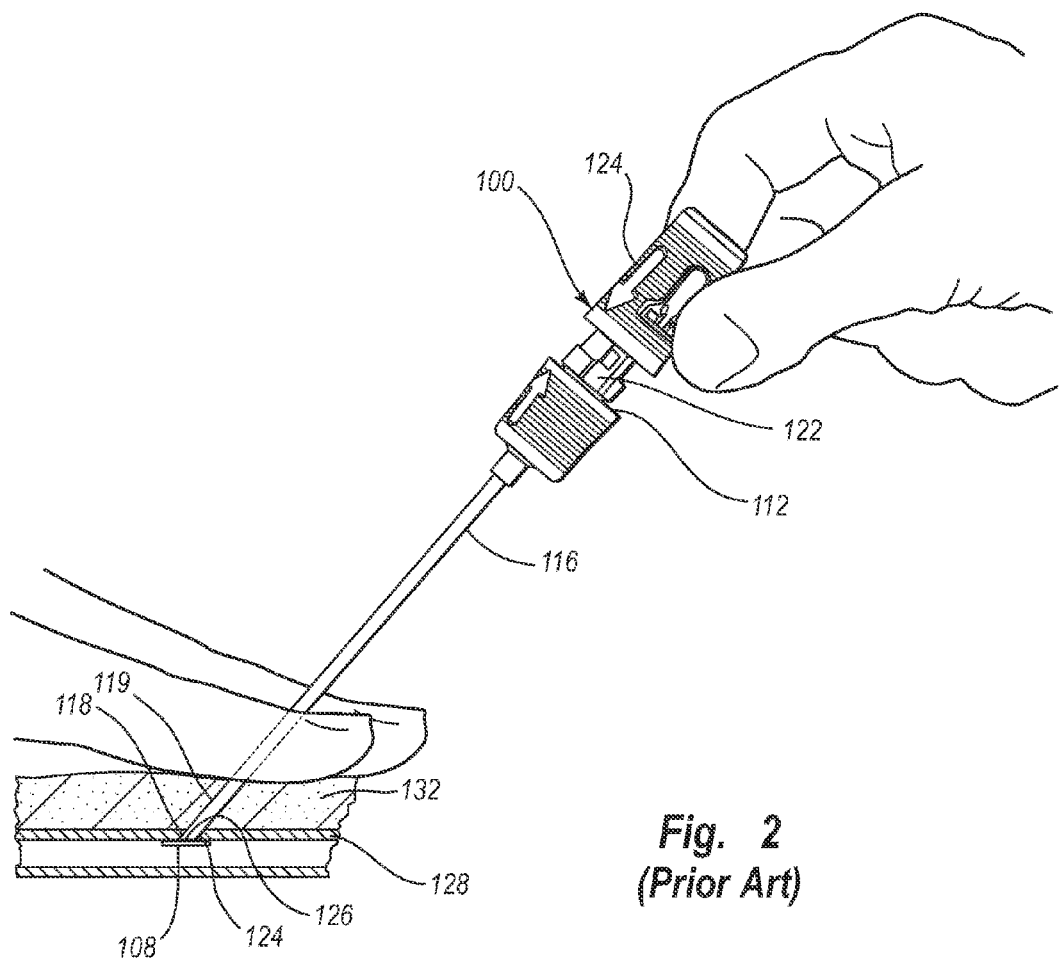
FIG. 2 is a side view of the tissue closure device of FIG. 1 inserted into an insertion sheath and engaged with an artery.
Figure 3:
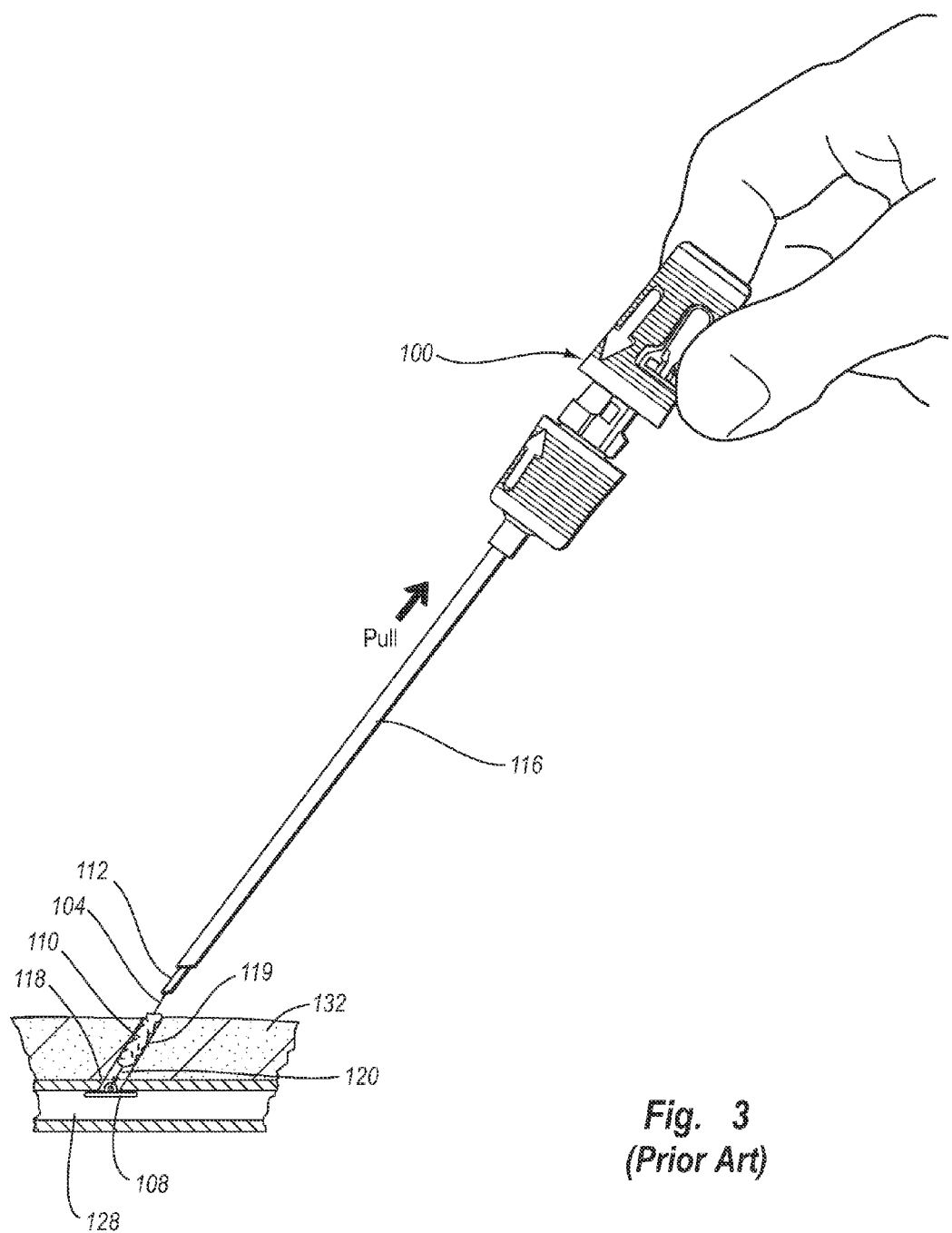
FIG. 3 is a side view of the tissue closure device and insertion sheath of FIG. 2 being withdrawn from an artery according to the prior art to deploy a collagen sponge.
Figure 4:
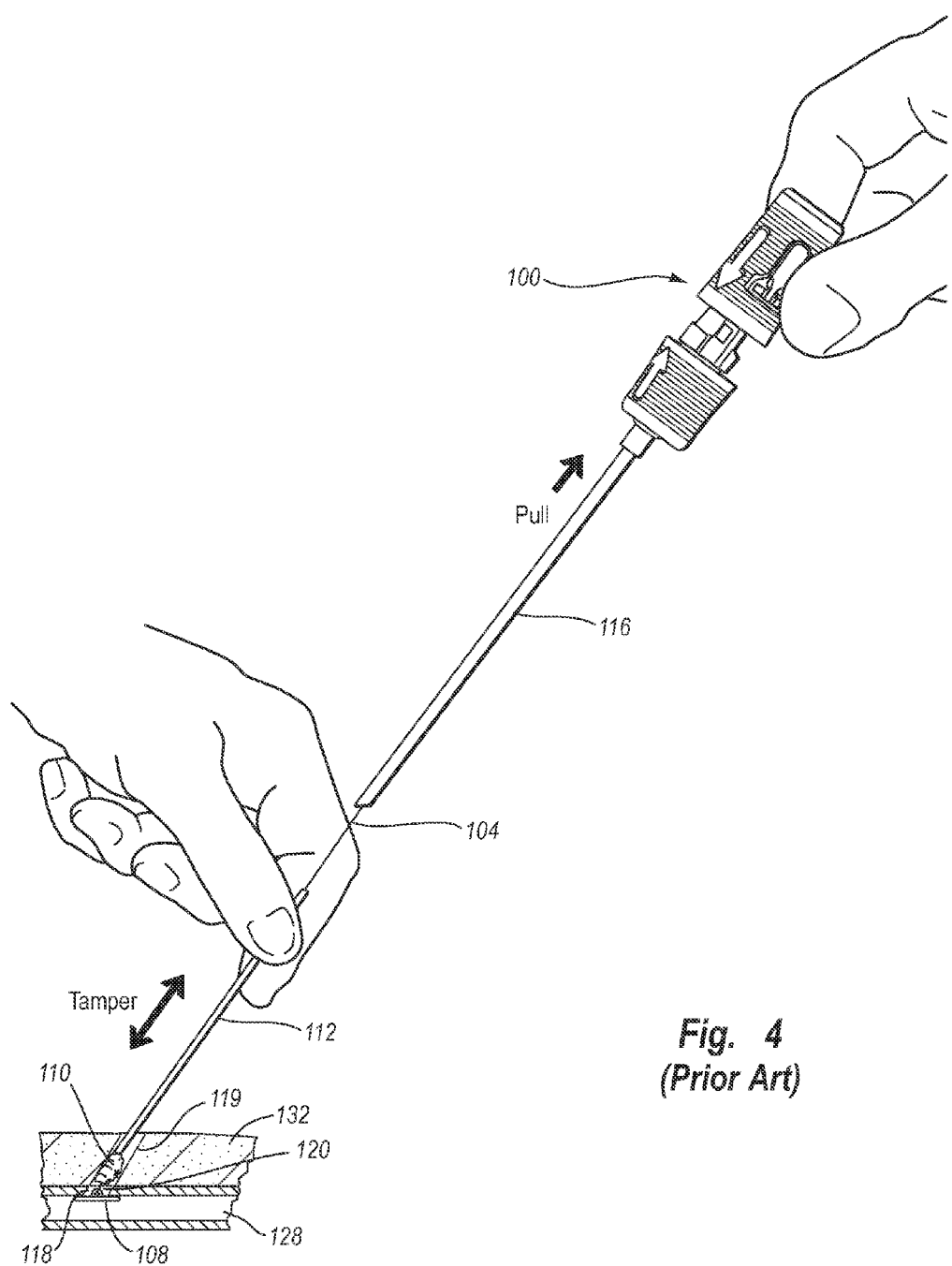
FIG. 4 is a side view of the tissue closure device of FIG. 1 illustrating manual compaction of the collagen sponge.

The insertion sheath 116 is shown in FIGS. 2-4 inserted through a percutaneous incision 119 and into an artery 128. The bypass tube 114 (see FIG. 1) may include an oversized head 120 that prevents the bypass tube 114 from passing through an internal passage of the insertion sheath 116. Therefore, as the puncture closure device 100 is inserted into the insertion sheath 116, the oversized head 120 bears against a proximal surface of a hub portion 117 of insertion sheath 116. Further insertion of the puncture closure device 100 results in sliding movement between the carrier tube 102 and the bypass tube 114, thereby releasing the anchor 108 from the bypass tube 114 (see FIG. 1). Typically, the anchor 108 remains in the flush arrangement shown in FIG. 1 following release from the bypass tube 114, limited in movement by the insertion sheath 116.

The vascular puncture closure device 100 may also include a housing 124 and a pair of sheath connection member 122 that extend distally from the housing 124. The sheath connection members 122 may be constructed to releasable connect the vascular puncture closure device 100 to the insertion sheath 116.

The insertion sheath 116 may include a monofold at a distal end thereof. The monofold acts as a one-way valve to the anchor 108. Typically, monofolds are a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, ejecting the collagen pad 110 from the carrier tube 102 into the percutaneous incision 119 and exposing the compaction member 112. Further withdrawal of the puncture closure device 100 fully exposes the compaction member 112 as shown in FIG. 4. The operator can then manually compact the collagen pad 110 while cinching together the anchor 108 and collagen pad 110 with the self-tightening slip-knot on the filament 102. Thus, the tissue puncture is sandwiched between the anchor 108 and the collagen pad 110, thereby sealing the tissue puncture 118. The filament 104 is then cut and the incision tract 119 may be closed. The filament 104, anchor 108, and collagen pad 110 are generally made of resorbable materials and therefore remain in place while the puncture 118 heals.

Using the typical tissue puncture closure device 100 described above, however, it may be difficult to eject and compact the collagen pad 110. The insertion sheath 116 resists deformation as the collagen pad 110 is ejected from the carrier tube and compaction may not commence until the sheath 116 has been removed. Under certain conditions, removal of the sheath 116 prior to compacting the collagen pad 110 may cause the collagen pad 110 to retract or displace proximally from the tissue puncture 118, creating an undesirable gap between the collagen pad 110 and the puncture 118. The gap may remain even after compaction, and sometimes results in only a partial seal and bleeding from the tissue puncture 118.

Therefore, the present specification describes a medical device such as a tissue puncture closure device that is capable of retracting a procedural sheath relative to a closure device, exposing a distal end of the closure device prior to ejecting a sealing pad. The closure device also automatically drives the sealing pad toward a tissue puncture upon withdrawal of the tissue puncture closure device from the tissue puncture site. The mechanism for automatically driving the sealing pad may be selectably disengagable.

As described above, the general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Referring now to FIGS. 5-12, a medical device, for example a tissue puncture closure device 200 (also referred to herein as "vascular closure device" and "closure device"), is shown according to one embodiment of the present disclosure. The closure device 200 is shown in an assembly view in FIG. 5 in combination with an insertion sheath 216 and inserted through a percutaneous incision 119 and vascular puncture 118. The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial or vascular) puncture. However, it will be understood that while the description of the embodiments below are directed to the sealing off of percutaneous punctures in vessels, such devices have much more wide-spread applications and can be used for sealing punctures or incisions in other types of tissue walls as well. Thus, the sealing of a percutaneous puncture in a vessel, shown herein, is merely illustrative of one particular use of the closure device 200 of the present disclosure.

The closure device 200 includes a first or proximal end portion 206 and a second or distal end portion 207. A carrier tube 202 extends from the proximal end portion 206 to the distal end portion 207 and includes an outlet 213 at the distal end portion 207. The distal end portion 207 may include a slit (not shown) that facilitates ejection of a sealing pad 210 from the carrier tube 202.

The carrier tube 202 may be made of plastic or other material and is designed for insertion through the procedure sheath 216. The procedure sheath 216 is designed for insertion through a percutaneous incision 219 and into the vessel 128. In at least one example, the vessel 128 is a femoral artery.

An anchor 208 and a sealing pad 210 may be positioned at the distal end portion 207 of the closure device 200. The anchor 208 of the present embodiment may be an elongated, relatively stiff, low-profile member arranged to be seated inside the vessel 128 against an internal vessel wall contiguous with the vessel puncture 118. The anchor 208 typically comprises a biologically resorbable polymer. The sealing pad 210 may be formed of, for example, a compressible sponge, foam, or fibrous mat made of a non-hemostatic biologically resorbable material such as collagen. The sealing pad 210 may be configured in any shape so as to facilitate sealing the vascular puncture 118.

The sealing pad 210 and anchor 208 are connected to one another by a suture or filament 204. The filament 204 also typically comprises a biologically resorbable material. The anchor 208, the sealing pad 210, and the filament 204 are collectively referred to as the "closure elements" below.

Figures 5, 6:
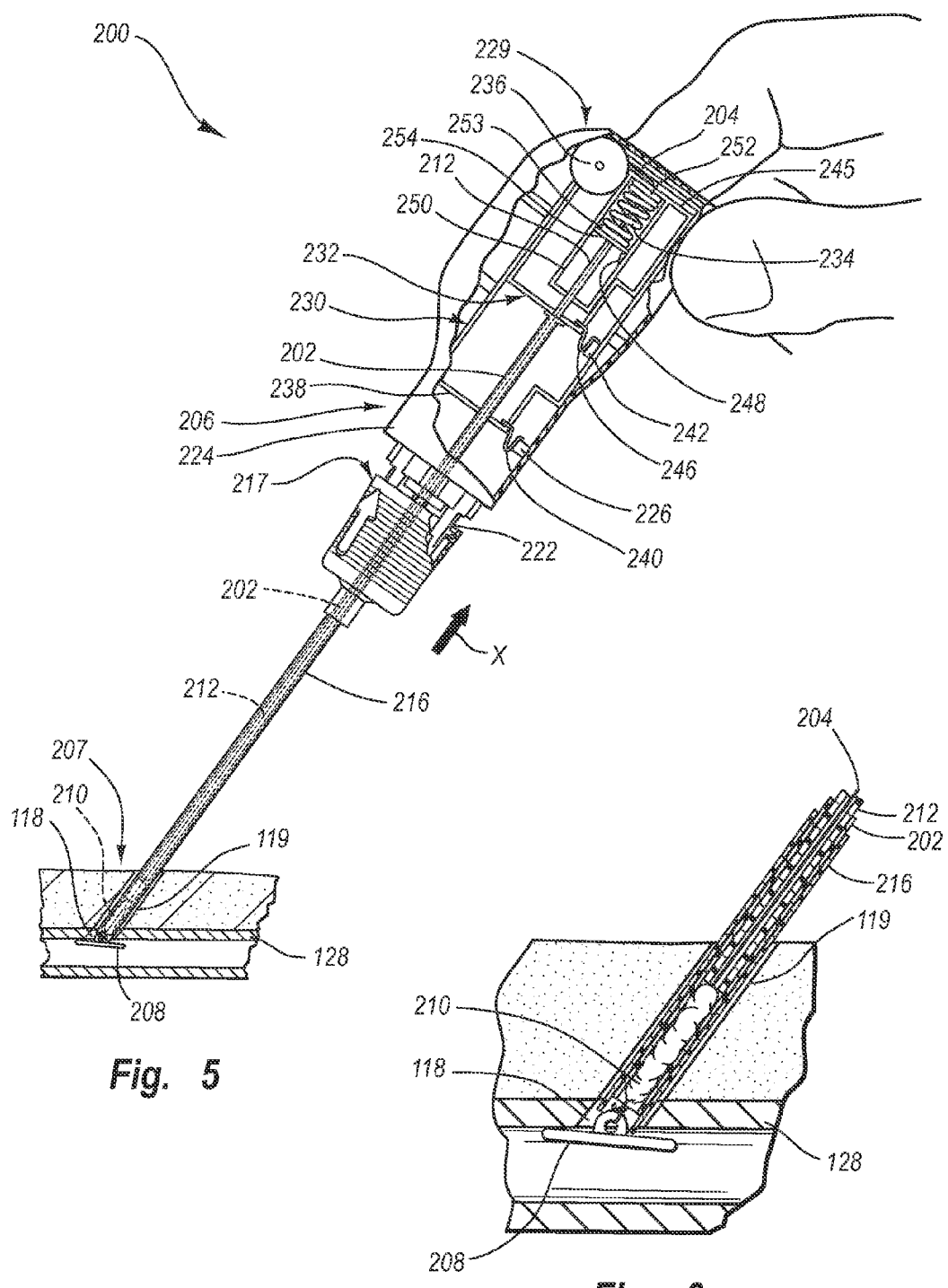
FIG. 5 is a perspective view of an example tissue puncture closure device having an automatic compaction mechanism according to the present disclosure, the tissue puncture closure device being inserted into an insertion sheath and shown engaged with an artery in a first position.
FIG. 6 is a detailed inset of FIG. 5.

As shown in FIGS. 5-6, the anchor 208 is initially arranged adjacent to and exterior of the distal end portion 207 of the carrier tube 202, while the sealing pad 210 is initially disposed within the carrier tube 202. The anchor 208 is shown nested in its low profile configuration along the carrier tube 202 to facilitate insertion into the vessel 128. The filament 204 extends distally from the first end portion 206 of the closure device 200 through the carrier tube 202. The filament 204 may be threaded through one or more perforations in the sealing pad 210, through a hole in the anchor 208, and proximally back toward the carrier tube 202 to the sealing pad 210. The filament 204 is preferably threaded again through a perforation or series of perforations in the sealing pad 210. The filament 204 may also be threaded around itself to form a self-tightening slip-knot. The filament 204 may thus connect the anchor 208 and the sealing pad 210 in a pulley-like arrangement to cinch the anchor 208 and the sealing pad 210 together when the carrier tube 202 is pulled away from the anchor 208 and the sealing pad 210. The anchor 208 and the sealing pad 210 sandwich and lock the anchor and plug together, sealing the tissue puncture 218.

The carrier tube 202 houses a compaction member, such as a compaction member 212 configured to advance the sealing pad 210 along the filament 204 and toward the anchor 208. The compaction member 212 is shown located partially within the carrier tube 202 and proximal of the sealing pad 208. The compaction member 212 also extends through a housing 224 of the closure device 200. The compaction member 212 is preferably an elongated tubular or semi-tubular member that may be rigid or flexible and formed of any suitable material. For example, according to one embodiment, the compaction member 212 comprises a polyurethane material. The filament 204 extends through at least a portion of the compaction member 212. For example, as shown in FIGS. 5-12, the filament 204 extends along the compaction member 212 between the first and second end portions 206, 207. Typically, the filament 204 is not directly connected to the compaction member 212. Accordingly, the filament 204 and the compaction member 212 may slide past one another.

According to the embodiment of FIGS. 5-12, the filament 204 extends proximally into the housing 224 and is collected onto a filament spool 236 of an automatic compaction assembly 229. The automatic compaction assembly further includes a first slide 230, a second slide 232, and a biasing member 234. The biasing member 234 and filament spool 236 are carried by the second slide 232. The second slide 232 is carried by and slidable relative to the first slide 230. The first slide 230 is slidably mounted in the housing 224 of the closure device 200. The housing 224 may include a first release surface 226 arranged to contact a portion of the first slide 230 as described in further detail below.

The first slide 230 includes a distal end 238, a first release member 240, and a second release surface 242. The first slide 230 is arranged within the housing 224 and is movable between at least the retracted or first position shown in FIG. 5 and the extended or second position shown in FIG. 7. The first slide 230 maintains the retracted position during insertion of the closure device 200 into the insertion sheath 216 and insertion into the vessel 128 (see FIG. 5).

The first slide 230 is held in the retracted position with a release mechanism. The release mechanism may include, for example, the first release member 240 and the first release surface 226. Typically, the first release member 240 engages the first release surface 226 to hold the first slide 230 in the retracted position until at least one of the first release member 240 and first release surface 226 is activated. The activation of the first release member 240 or the first release surface 226 may occur automatically upon application of a predetermined amount of force applied in an axial direction (i.e., a direction along the length dimension of insertion sheath 216) to the first slide 230. The force in the axial direction can be applied by withdrawing the closure device 200 and sheath 216 in the direction X while the anchor 208 is engaged with an inner surface of the vessel 128 as shown in FIG. 5. This predetermined amount of axially applied force provides disengagement of the first release member 240 from the first release surface 226.

The predetermined amount of force applied in the axial direction to the first slide 230 to provide automatic movement of the first slide 230 relative to the housing 224 is typically in the range of about 0.3 lbs to about 2.0 lbs., and more preferably in the range of about 0.3 lbs. to about 1.0 lbs. Typically, the predetermined amount of force applied in the axial direction to the first slide 230 is no greater than about 1.0 lbs.

Figures 7, 8:
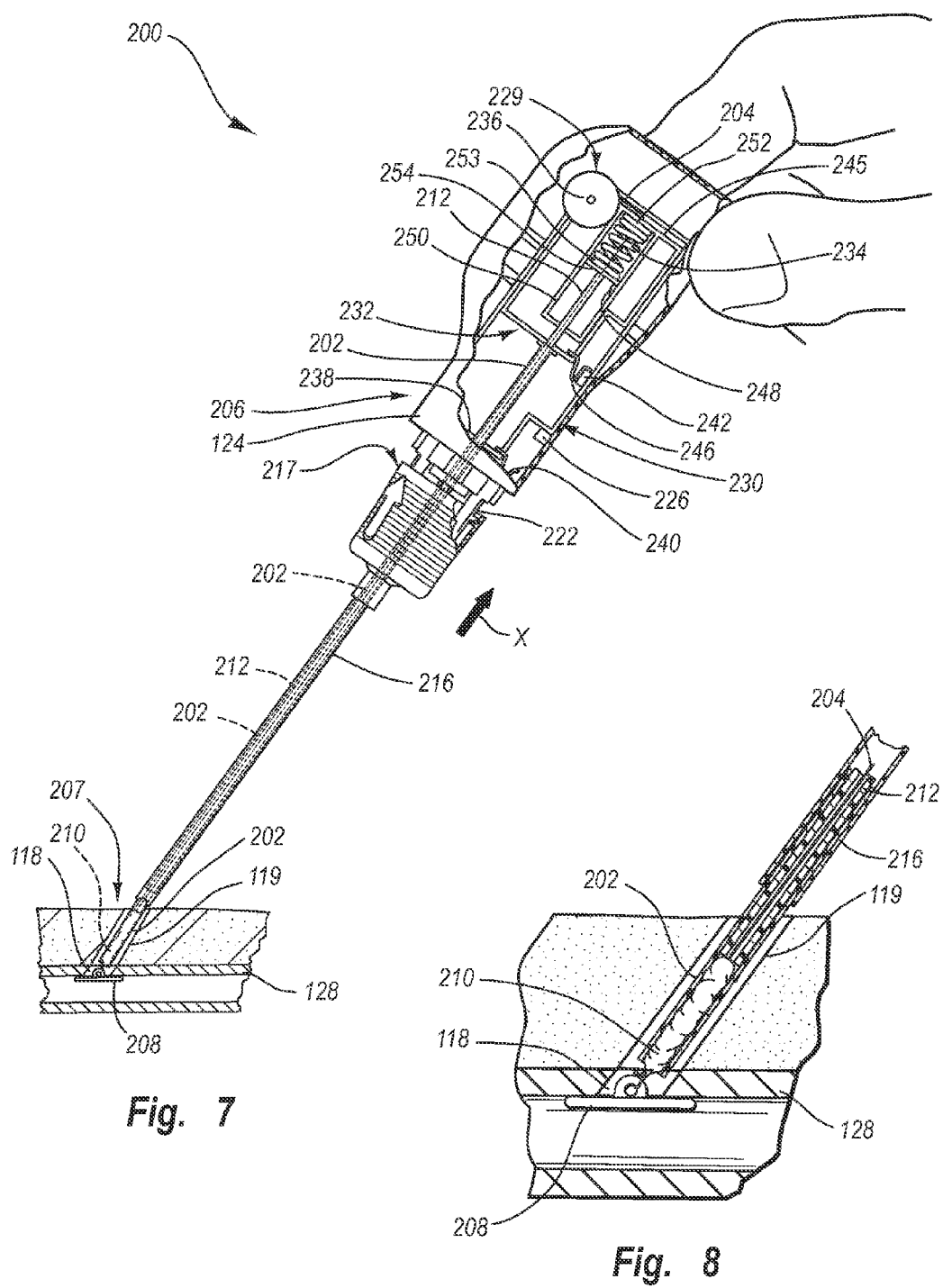
FIG. 7 is a side view of the tissue closure device and insertion sheath of FIG. 5 shown engaged with an artery in a second position with the procedure sheath retracted.
FIG. 8 is a detailed inset of FIG. 7.

By permitting the first slide 230 to move from the retracted position shown in FIG. 5 to the advanced position shown in FIG. 7, the entire automatic compaction assembly 229, carrier tube 202 (which is connected to the second slide), and compaction member 212 (which is connected to the biasing member 234) are able to maintain substantially the same position relative to the vessel puncture 118 while the housing 224 and insertion sheath 216 move proximally in the direction X relative to the vessel puncture 118. In at least one example, the insertion sheath 216 is removed from the vessel puncture 118 and percutaneous incision 119, and the carrier tube 202 remains in the percutaneous incision 119 when the first slide 230 moves from the retracted position shown in FIG. 5 to the advanced position shown in FIG. 7.

The second slide 232 includes distal and proximal ends 244, 245, a second release member 246, a third release surface 248, and a biasing member track 250. The second slide 232 is arranged within the housing 224 and is movable between at least the retracted or first position shown in FIGS. 5 and 7 and the extended or second position shown in FIGS. 9 and 11. The second slide 232 maintains the retracted position during insertion of the closure device 200 into the insertion sheath 216 and into the vessel 128 (see FIG. 5), retraction of the housing 224 and insertion sheath 216 in the direction X to the position shown in FIG. 7, and movement of the first slide into the advanced position shown in FIG. 7.

The second slide 232 is held in the retracted position with a release mechanism. The release mechanism may include, for example, the second release member 246 and the second release surface 242. Typically, the second release member 246 engages the second release surface 242 of the first slide 230 to hold the second slide 232 in the retracted position until at least one of the second release member 246 and second release surface 242 is activated. The activation of the second release member 246 and second release surface 242 may occur automatically upon application of a predetermined amount of force applied in the axial direction (i.e., a direction along the length dimension of insertion sheath 216) to the second slide 232. The force in the axial direction can be applied by withdrawing the closure device 200 and sheath 216 in the direction X while the anchor 208 is engaged with an inner surface of the vessel 128 and the first slide 230 is positioned in the advanced position shown in FIG. 7. This predetermined axially applied force provides disengagement of the second release member 246 from the second release surface 242.

The predetermined amount of force applied in the axial direction to the second slide 232 to provide automatic movement of the second slide 232 relative to the first slide 230 is typically in the range of about 0.3 lbs to about 2.0 lbs., and more preferably in the range of about 0.3 lbs. to about 1.0 lbs. Typically, the predetermined amount of force applied in the axial direction to the second slide 232 is no greater than about 1.0 lbs.

Figures 9, 10:
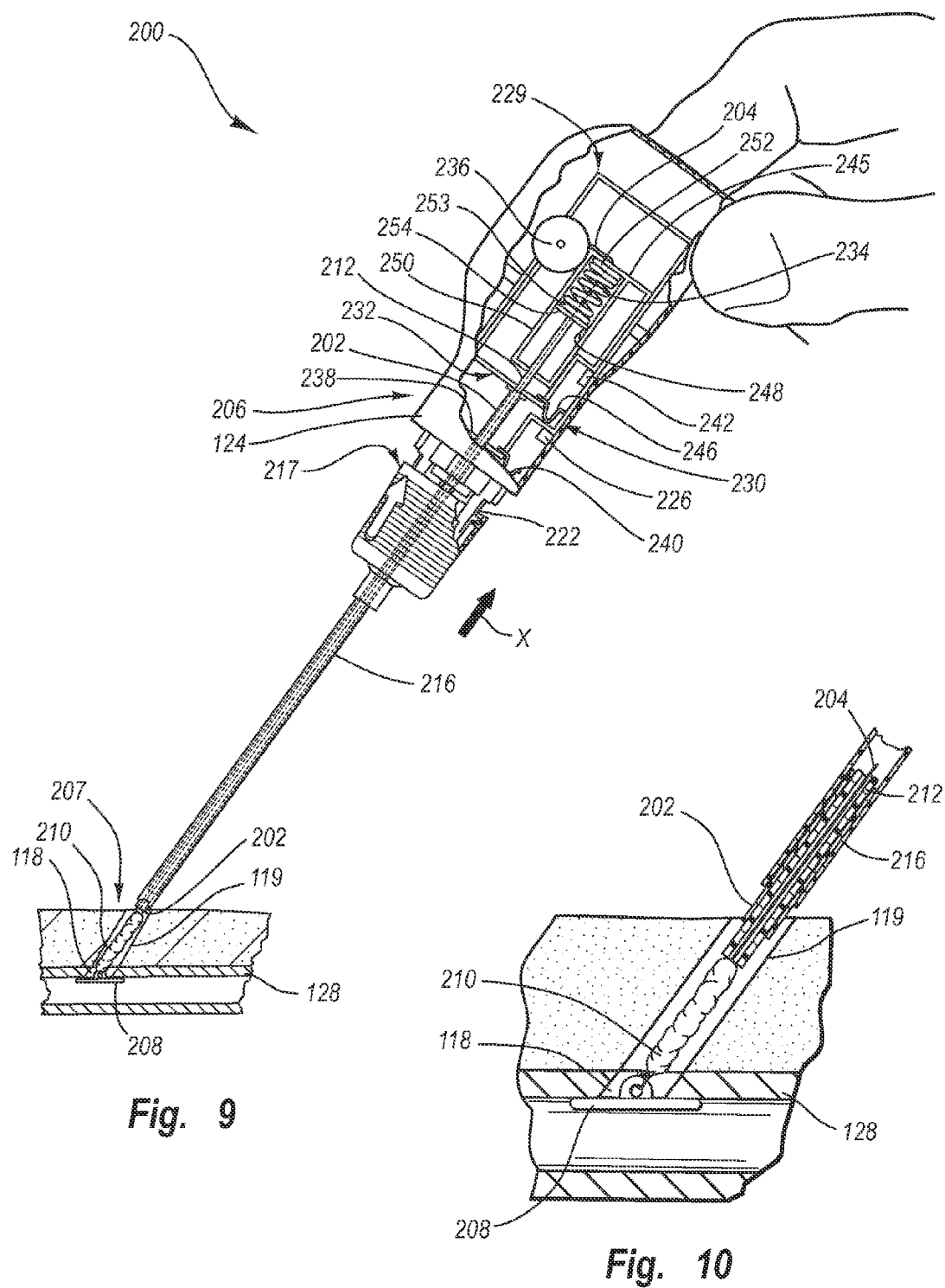
FIG. 9 is a side view of the tissue closure device and insertion sheath of FIG. 5 shown engaged with an artery in a third position with the carrier tube retracted.
FIG. 10 is a detailed inset of FIG. 9.

The carrier tube 202 is typically connected to the second slide 232 and the compaction member 212 is typically connected to the biasing member 234. By permitting the second slide 232 to move from the retracted position shown in FIGS. 5 and 7 to the advanced position shown in FIG. 9 while maintaining the biasing member in a compacted state as shown in FIG. 9, the compaction member 212 is able to maintain substantially the same position relative to the vessel puncture 118 while the housing 224, insertion sheath 216, and carrier tube 202 move proximally in the direction X relative to the vessel puncture 118. In at least one example, the carrier tube 202 is removed from the vessel puncture 118 and percutaneous incision 119 when the second slide 232 moves from the retracted position shown in FIG. 7 to the advanced position shown in FIG. 9.

The biasing member 234 is positioned in the housing 224 and carried by the second slide 232. In at least some arrangements, the biasing member 234 is positioned in the biasing member track 250. The biasing member track 250 may help maintain alignment of the biasing member 234 relative to the compaction member 212. The biasing member 234 is movable from a compressed or first position shown in FIGS. 5, 7 and 9, to an extended or second position shown in FIG. 11. The biasing member 234 maintains the compressed position during insertion of the closure device 200 into the insertion sheath 216 and into the vessel 128 (see FIG. 5), retraction of the housing 224 and insertion sheath 216 in the direction X to the position shown in FIG. 7, movement of the first slide into the advanced position shown in FIG. 7, further retraction of the housing 224 and insertion sheath 216 in the direction X to the position shown in FIG. 9, and movement of the second slide 232 into the advanced position shown in FIG. 9.

The biasing member 234 is held in the compressed position with a release mechanism. The release mechanism may include the third release member 254 and the third release surface 248. Typically, the third release member 254 engages the third release surface 248 of the second slide 232 to hold the biasing member 234 in the retracted position until at least one of the third release member 254 and third release surface 248 is activated. The activation of the third release member 254 and third release surface 248 may occur automatically upon application of a predetermined amount of force applied in the axial direction (i.e., a direction along the length dimension of insertion sheath 216) to the biasing member 234. The force in the axial direction may be applied by withdrawing the closure device 200 and sheath 216 in the direction X while the anchor 208 is engaged with an inner surface of the vessel 128, the first slide 230 is positioned in the advanced position shown in FIG. 7, and the second slide 232 is positioned in the advanced position shown in FIG. 9. This predetermined axially applied force provides disengagement of the third release member 254 from the third release surface 248.

The predetermined amount of force applied in the axial direction to the biasing member 234 provides automatic release of the biasing member 234 to expand from the compressed state shown in FIGS. 5, 7 and 9 to an expanded state shown in FIG. 11 to apply an axially directed force in the direction Y to the compaction member (see FIG. 11). The predetermined amount of force needed to release the biasing member 234 is typically in the range of about 0.3 lbs to about 2.0 lbs., and more preferably in the range of about 0.3 lbs. to about 1.0 lbs. Typically, the predetermined amount of force need to release the biasing member is no greater than about 1.0 lbs. The amount of axially force applied by the biasing member 234 to the compaction member 212 in the direction Y is typically in the range of about 0.3 lbs to about 2.0 lbs., and more preferably in the range of about 0.3 lbs. to about 1.0 lbs. Typically, the axial force applied by the biasing member to the compaction member 212 is no greater than about 1.0 lbs.

As discussed above, the biasing member 234 may be an extension spring, a constant force spring, or a coil spring instead of a compression spring. At least some features of the device 200 may require rearranging or modification to accommodate extension, constant force, and coil springs. In some arrangements, multiple compression, extension, constant force, or coil springs may be used as the biasing member 234. In other arrangements, a combination of any two or more of a compression, extension, constant force, and coil spring may be used as the biasing member 234.

The first and second slides 230, 232 and the biasing member 234 are configured to automatically release to move relative to the housing 224 or to each other upon application of a predetermined amount of force applied in the axial direction, as described above. The predetermined amount of force for release of each of the first and second slides 230, 232 and the biasing member 234 may be different. For example, the predetermined amount of force may be least for release of the first slide 230, a greater amount for the second slide 232, and an even greater amount for the biasing member 234. In some arrangements, the second slide 232 is not able to release until after the first slide 230 has been released, and the biasing member 234 is not able to release until after the first and second slides 230, 232 have been released.

In other arrangements, at least one of the first and second slides 230, 232 and the biasing member 234 are released manually to move relative to the housing 224 or to each other by the operator of closure device 200 activating a release mechanism. In some arrangements, the closure device 200 includes visual or audible features that indicate to the operator when features of the closure device 200 have attained certain positions. For example, the closure device 200 may include a window into the housing 224 and at least one position marker so the operator can see when the first slide 230 has reached the advanced position shown in FIG. 7, which indicates to the operator that the second slide can be released manually.

In practice, the carrier tube 202 (containing the closure elements described above) of the closure device 200 is inserted into the insertion sheath 216, which is already inserted within the vessel 128. As the closure device 200 and the associated closure elements are inserted into the procedure sheath 216, the anchor 208 passes through and out of the distal end of the procedure sheath 216 and is inserted into the vessel 128. As mentioned above and shown in FIG. 5, the anchor 208 is initially arranged substantially flush with the carrier tube 202 to facilitate insertion of the anchor 208 through the percutaneous incision 119 and into the vessel 128.

After the anchor 208 passes out of the distal end of the procedure sheath 216, however, the anchor 208 tends to deploy or rotate to the position shown in FIGS. 5-6. The closure device 200 may be partially withdrawn, catching the anchor 208 on the distal end of the insertion sheath 216 and rotating the anchor 208 to the position shown in FIGS. 5-6. The closure device 200 typically includes a pair of sheath connection members 222 that are lockingly received by a matching pair of recesses (not shown) in a proximal surface of the hub portion 217 of the procedure sheath 216. The locking arrangement between the sheath connection members 222 and matching recesses in the insertion sheath 216 fixes the position of the housing 224 relative to the procedure sheath 216.

Following deployment of the anchor 208, the housing 224 and the insertion sheath 216 are withdrawn together. Withdrawing the housing 224 a first retraction distance causes the anchor 208 to anchor itself against an internal wall of the vessel 128. With the anchor 208 anchored within the vessel 128, retracting the housing 224 and insertion sheath 216 in the direction X a second retraction distance releases the first slide 230 to permit relative movement between the housing 224 and the first slide 230 that results in the insertion sheath 216 retracting out of the percutaneous incision 119 (see FIGS. 5-8). The housing 224 and insertion sheath 216 are retracted the second retraction amount in the direction X until the first slide reaches the advanced position in the housing 224 shown in FIG. 7.

Retracting the housing 224 and insertion sheath 216 a third retraction distance after completion of retracting the second retraction distance tends to pull the sealing pad 210 out from the distal end portion 207 of the carrier tube 202, thereby depositing the sealing pad 210 within the percutaneous incision 119. The slit (not shown) in the carrier tube 202 may provide improved ease in ejecting the sealing pad 210.

As described above, the carrier tube 202 is connected to the second slide 232 and the compaction member 212 is connected to the biasing member 234. Applying a retraction force in the direction X after retracting the second retraction distance releases the second slide 232 to move axially relative to the first slide 230 so that the compaction member maintains the same position relative to the percutaneous incision 119 and the carrier tube 202 retracts out of the percutaneous incision 119 to expose the sealing pad 210 (see FIG. 10). Retracting the housing 224 and insertion sheath 216 the third retraction distance moves the second slide from the position shown in FIG. 7 to the advanced position shown in FIG. 9.

Applying a retraction force to the housing 224 in the direction X after the housing 224, insertion sheath 216, and carrier tube 202 have been retracted the second retraction distance, releases the biasing member 234 to advance the compaction member 212 distally in the direction Y (see FIGS. 11-12). The filament spool 236 may apply tension to the filament 204 to pull the filament 204 in a direction away from the anchor 208 and sealing pad 210 as the housing 224 is retracted in the direction X through the first, second and third retraction distances. The tension in the filament applied by the filament spool 236 may cinch and lock (with a slip knot or the like) together the anchor 208 and the sealing pad 210, sandwiching a wall of the vessel 128 between the anchor 208 and sealing pad 210. The force exerted by the compaction member 212 and the cinching together of the anchor 208 and sealing pad 210 by the filament 204 also causes the sealing pad 210 to deform radially outward within the percutaneous incision 119 and function as an anchor on the proximal side of the vascular incision 118 as shown in FIGS. 11-12.

When the sealing pad 210 has been sufficiently compacted, the automatic compaction assembly 229 may be disengaged, enabling further retraction of the closure device 200 without additional compaction. With the sealing pad 210 fully compacted, there may be little or no portion of the filament 204 extending outside of the tissue layer 230 and exposed to an operator. Therefore, it may be difficult for an operator to separate the sealing pad 210 and anchor 208 from the remainder of the closure device 200. In one example, the automatic compaction assembly 229 is disengaged by releasing the filament spool 236 to permit the filament 204 to fully unwind from the filament spool 236. Unwinding the filament spool 236 exposes a sufficient length of the filament 204 to allow an operator to easily cut the filament 204 and separate the sealing pad 210 and anchor 208 from the remainder of the closure device 200.

It may be desirable in some cases to increase or decrease the linear velocity of the compaction member 212 relative to the sealing pad 210 to improve compaction of the sealing pad 210. The biasing member 234 may have various constructions that provide optimization of the linear velocity of the compaction member 212 and other performance characteristics such as the amount of force applied and the axial distance traveled by the compaction member 212 relative to the sealing pad 210.

The sealing pad 210 is shown in FIGS. 5-12 having a generally elongate, cylindrical structure. Other constructions are possible for the sealing pad used with the closure devices disclosed herein. Some example alternative sealing pad constructions for use with the closure devices disclosed herein are described in U.S. Published Patent Application No. 2005/0125031, which application is hereby incorporated in its herein by this reference.

Figure 13:
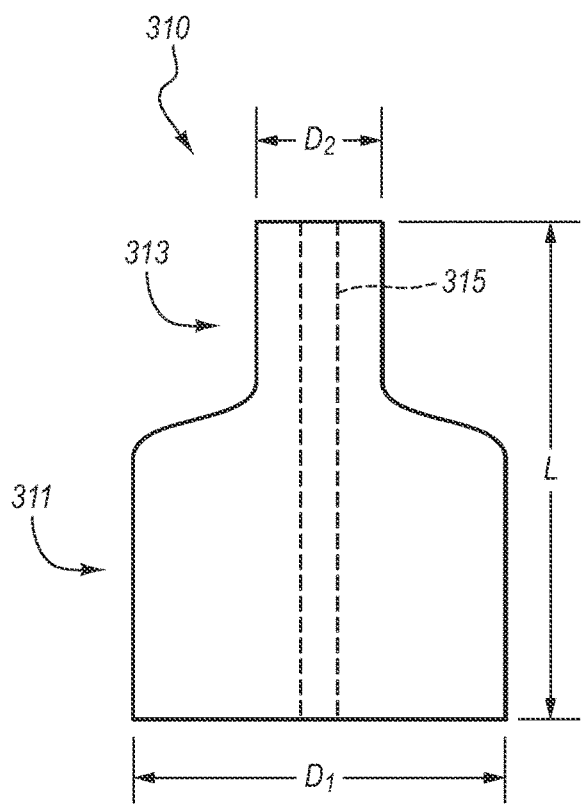
FIG. 13 is a side view of an example sealing pad according to the present disclosure for use with the tissue closure device of FIG. 5.
Figure 14:
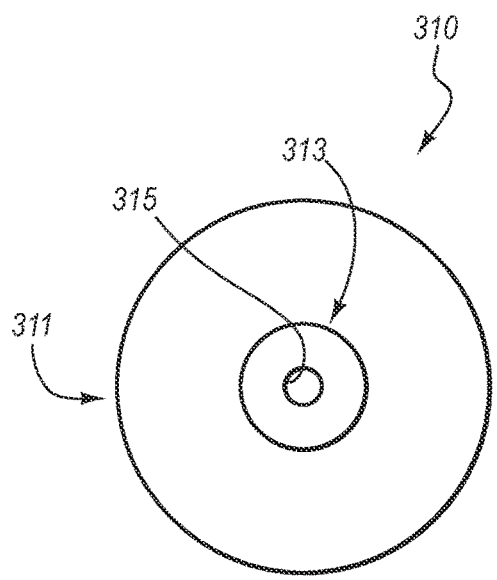
FIG. 14 is an end view of the sealing pad of FIG. 13.

FIGS. 13-14 illustrate another example sealing pad 310. The sealing pad 310 includes a distal portion 311, a proximal portion 313, and a filament aperture 315. The distal portion 311 includes a maximum diameter or dimension $D_1$, and the proximal portion 313 has a maximum diameter or dimension $D_2$. The dimension $D_1$ may be greater than the diameter of typical sealing pads, such as the sealing pads 110, 210 described with reference to FIGS. 1-12. The greater dimension $D_1$ may provide improved coverage of the vascular incision 118 and resulting hemostasis. The dimension $D_2$ may be smaller then the diameter of typical sealing pads, such as the sealing pads 110, 210. Providing the proximal portion 313 with a smaller dimension $D_2$ and the distal portion 311 with a larger dimension $D_1$ may provide easier compaction of the sealing pad 310 for at least the reason that the shape of sealing pad 310 before compaction is closer to a desired shape of the sealing pad after completion of compaction.

The sealing pad 310 also has a length dimension L. The length L may be less than a length of typically sealing pad, such as the sealing pads 110, 210. The shorter length L reduces the chances of the proximal portion 313 remaining outside of the percutaneous incision 119 after compaction by the compaction member 212 is complete regardless of the depth of the percutaneous incision. In circumstances where the sealing pad 310 is ejected from the carrier tube at a location outside or partially outside of the percutaneous incision 119, the shorter length L may provide less compaction force being required to force the sealing pad 310 into the percutaneous incision 119.

The sealing pad 310 may have a cylindrical shape with a circular cross-section, wherein the cross-section increases from the proximal portion 313 to the distal portion 311. The sealing pad 310 may have other cross-sectional shapes and different constructions in other embodiments. For example, the sealing pad 310 may have a rectangular or elliptical cross-sectional shape. In other examples, the sealing pad 310 is tapered along its length from a proximal end to a distal end. The taper may be a linear taper. The sealing pad 310 may include a curved portion, a step portion, or a combination of constant cross-sectional sized portions and variable cross-sectional sized portions along the length L.

Figure 15:
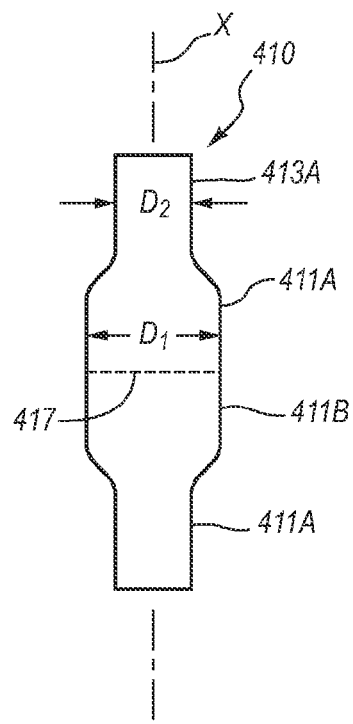
FIG. 15 is a side view of an example sealing pad according to the present disclosure for use with the tissue closure device of FIG. 5.
Figure 16:
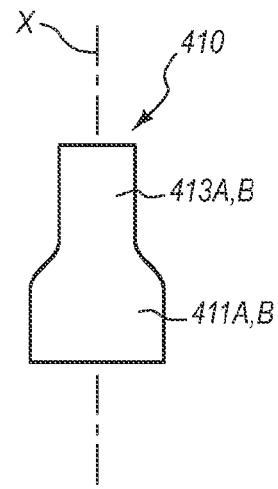
FIG. 16 is an end view of the sealing pad of FIG. 15.

FIGS. 15-29 illustrate additional sealing pads embodiments in accordance with the present disclosure. FIGS. 15-16 illustrate a sealing pad 410 that includes distal portions 411A-B and proximal portions 413A-B. The distal portions 411A-B and proximal portions 413A-B are centered about a longitudinal axis X. The sealing pad 410 is shown in an unfolded state in FIG. 15. The sealing pad 410 is foldable in half about a fold line 417 into a folded state as shown in FIG. 16. Typically, the distal portions 411A-B are substantially the same size and the proximal portions 413A-B are substantially the same size.

Figure 17:
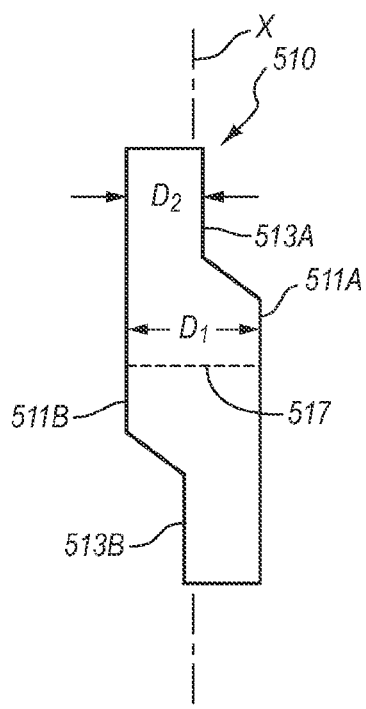
FIG. 17 is a side view of an example sealing pad according to the present disclosure for use with the tissue closure device of FIG. 5.
Figure 18:
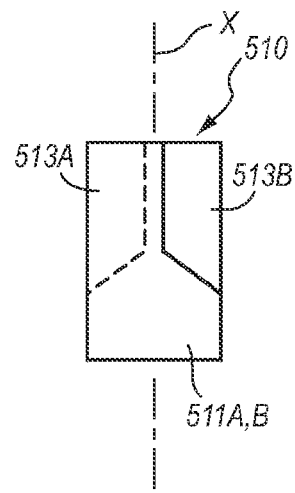
FIG. 18 is an end view of the sealing pad of FIG. 17.

FIGS. 17-18 illustrate a sealing pad 510 that includes distal portions 511A-B and proximal portions 513A-B. The distal portions 511A-B are centered about a longitudinal axis X, and the proximal portions 513A-B are offset from the longitudinal axis X. The sealing pad 510 is shown in an unfolded state in FIG. 17. The sealing pad 510 is foldable in half about a fold line 517 into a folded state as shown in FIG. 18. Typically, the distal portions 511A-B are substantially the same size and the proximal portions 513A-B are substantially the same size so that when folded substantially overlap each other.

FIGS. 19-20 illustrate a sealing pad 610 that includes distal portions 611A-B and a proximal portion 613. The distal portions 611A-B and proximal portion 613 are centered about a longitudinal axis X. The sealing pad 610 is shown in an unfolded state in FIG. 19. The sealing pad 610 is foldable about a fold line 617 into a folded state as shown in FIG. 20. Typically, the distal portions 611A-B are substantially the same size so that when folded substantially overlap each other.

FIGS. 21-22 illustrate a sealing pad 710 that includes distal portions 711A-B that are coupled together as a single piece, and proximal portions 713A-B that are separated from each other and from the distal portions 711A-B. The sealing pad 710 is shown in an unfolded state in FIG. 21. The sealing pad 710 is foldable in half about a fold line 717. Typically, the distal portions 711A-B are substantially the same size and the proximal portions 713A-B are substantially the same size so that when the sealing pad 710 is folded will substantially overlap each other.

FIG. 22 shows the sealing pad 710 in a folded state with the distal portions 711A-B spaced apart or separated from the proximal portions 713A-B. The distal and proximal portions 711A-B and 713A-B may be coupled together with a filament 104 that passes through at least one of the distal portions 711A-B and at least one of the proximal portions 713A-B. At least one of the distal and proximal portions 711A-B and 713A-B may include a filament aperture such as the filament aperture 315 described above with reference to FIGS. 15-16 through which the filament 104 passes.

FIGS. 23-24 illustrate a sealing pad 810 that includes distal portions 811A-B that are coupled together as a single piece, and proximal portions 813A-B that are coupled together as a single piece. The sealing pad 810 is shown in an unfolded state in FIG. 23. The distal portions 811A-B are foldable in half about a fold line 817A. The proximal portions 813A-B are folded about a fold line 817B. Typically, the distal portions 811A-B are substantially the same size and the proximal portions 813A-B are substantially the same size so that when the sealing pad 810 is folded will substantially overlap each other.

FIG. 24 shows the sealing pad 810 in a folded state with the distal portions 811A-B spaced apart or separated from the proximal portions 813A-B. The distal and proximal portions 811A-B and 813A-B may be coupled together with a filament 104 that passes through at least one of the distal portions 811A-B and at least one of the proximal portions 813A-B. At least one of the distal and proximal portions 811A-B and 813A-B may include a filament aperture such as the filament aperture 315 described above with reference to FIGS. 15-16 through which the filament 104 passes.

The distal portions 411A-B, 511A-B, 611A-B, 711A-B, 811A-B each have a maximum dimension $D_1$. The proximal portions 413A-B, 513A-B, 613, 713A-B, 813A-B have a maximum dimension $D_2$. The dimension $D_1$ may be greater than a maximum width dimension or diameter of typical sealing pads, such as the sealing pads 110, 210 described with reference to FIGS. 1-12. The greater dimension $D_1$ may provide improved coverage of the vascular incision 118 and resulting hemostasis. The dimension $D_2$ may be smaller then the maximum width dimension or diameter of typical sealing pads, such as the sealing pads 110, 210.

FIGS. 25-29 illustrate a sealing pad 910 that includes distal portions 911A-B and proximal portions 913A-B that are coupled together as a single piece. The sealing pad 910 is shown in an unfolded state in FIG. 25. The sealing pad 910 is foldable in half about a fold line 917 into a folded state as shown in FIG. 26. The distal portions 911A-B are shown having a size that is substantially the same as a size of the proximal portions 913A-B.

The distal portions 911A-B may comprise a first swelling additive that provide swelling in the Y direction from a size $D_1$ (see FIG. 28) to a size $D_3$ (see FIGS. 27 and 29). The proximal portions 913A-B may comprise a second swelling additive that provides swelling in the Y direction from the size $D_1$ (see FIG. 28) to a size $D_4$ (see FIGS. 27 and 29). Typically, the size $D_3$ is greater than the size $D_4$ to provide improved coverage of the vascular incision 118 and resulting hemostasis. The dimension $D_4$ may be smaller then the maximum width dimension or diameter of typical sealing pads, such as the sealing pads 110, 210. Various swelling additives may be added to any of the sealing pad embodiments disclosed herein to modify a shape and size of the sealing pad when in use.

Figure 30:
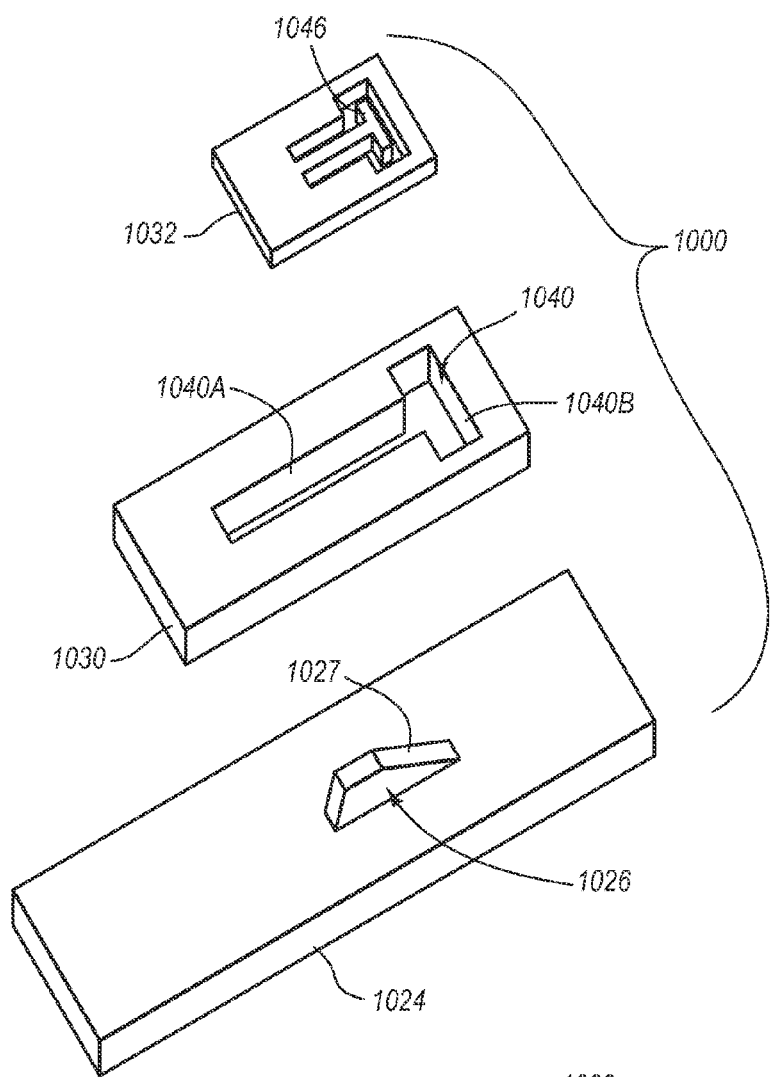
FIG. 30 is an exploded perspective view of an example release assembly according to the present disclosure for use with the tissue closure device of FIG. 5.
Figure 31:
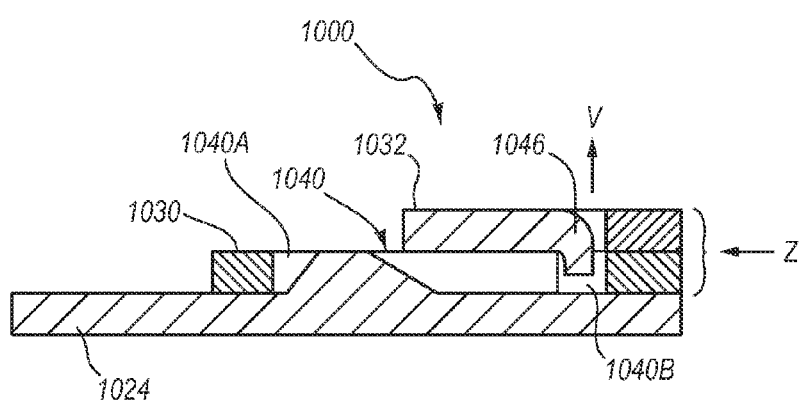
FIG. 31 is a cross-sectional view of the release assembly of FIG. 30.

FIGS. 30 and 31 illustrate an example release mechanism 1000 for use with the vascular closure devices disclosed herein. The release mechanism 1000 includes a housing portion 1024, a first slide portion 1030, and a second slide portion 1032. The housing portion 1024 includes a release protrusion 1026 having a tapered release surface 1027. The release protrusion 1026 may be positioned at any desired location along an inner surface of a housing (e.g., housing 224 described above) of the release mechanism 1000. The first slide 1030 includes a release aperture 1040 having a first opening 1040A sized to receive the release protrusion 1026 and a second opening 1040B sized to receive a portion of the second slide 1032. The second slide 1040B includes a release member 1046 that is configured to move into and out of the second opening 1040B of the first slide 1030.

In operation, the housing portion 1024, first slide 1030, and second slide 1032 are arranged in a stacked orientation as shown in FIG. 31. A portion of the release member 1046 extends into the second opening 1040B to restrict relative sliding movement between the first and second slides 1030, 1032. The release protrusion 1026 is arranged and configured so that the release surface 1027 contacts the release member 1046 as the first and second slides 1030, 1032 move in the Z direction to slide relative to the housing portion 1024. Contacting the release member 1046 with the release surface 1027 moves the release member 1046 in a direction V out of the release opening 1040 thereby permitting relative sliding movement between the first and second slides 1030, 1032.

The release protrusion 1026, release opening 1040, and release member 1046 may be arranged and configured to operate to release the first and second slides 1030, 1032 from each other when a predetermined force in the direction Z is applied. In at least one example, the predetermined amount of force is less than 1 lb.

Features similar to release protrusion 1026, release opening 1040, and release member 1046 may be used to provide release of a first slide from a housing, to provide release of a second slide relative to a first slide, or to provide release of a biasing member from a second slide of a vascular closure device such as those devices described herein. The features shown and described with reference to FIGS. 30-31 are merely exemplary of many other release mechanism that are possible for use with a vascular closure device to permit relative movement between features that are otherwise locked together.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device for partial insertion into and sealing of an internal tissue wall puncture, comprising:

(a) a filament extending from a first end of the closure device to a second end of the closure device;
(b) an anchor for insertion through the tissue wall puncture attached to the filament at the second end of the closure device;
(c) a sealing pad slidingly attached to the filament at the second end of the closure device;
(d) an automatic driving mechanism comprising:
  (i) a compaction member;
  (ii) at least one slide member at the first end of the closure device;
  (iii) a biasing member carried by the at least one slide member and operable to distally advance the compaction member for automatically compacting the sealing pad toward the anchor upon withdrawal of the closure device from the internal tissue wall puncture; and
(e) a housing positioned at the first end of the closure device, the at least one slide member including a first slide positioned in and movable relative to the housing;
wherein the automatic driving mechanism further comprises a filament spool with a portion of the filament wound thereon, the filament spool being carried by the first slide.

2. A tissue puncture closure device according to claim 1, further comprising a second slide positioned in and movable relative to the housing, the first slide being carried by and movable relative to the second slide.

3. A tissue puncture closure device according to claim 2, wherein the automatic driving mechanism further includes first, second and third automatic release members operable upon withdrawal of the closure device from the internal tissue wall puncture, the first automatic release member operable to release the biasing member to advance the compaction member, the second release member operable to release the first slide to move between first and second positions relative to the housing, and the third automatic release member operable to release the second slide to move between first and second positions relative to the housing.

4. A tissue puncture closure device according to claim 3, wherein an amount of force to activate any one of the first, second and third automatic release members is no greater than about 1 lb.

5. A tissue puncture closure device according to claim 1, wherein the biasing member is arranged coaxially with the compaction member.

6. A tissue puncture closure device according to claim 1, wherein the biasing member is one of a compression, extension, constant force, or coil spring arranged in parallel with a direction of movement of the compaction member toward the sealing pad.

7. A tissue puncture closure device according to claim 1, wherein the automatic driving mechanism further includes at least one automatic release member operable to release the biasing member to advance the compaction member distally upon withdrawal of the closure device from the internal tissue wall puncture.

8. A tissue puncture closure device according to claim 7, wherein an amount of force applied upon withdrawal of the closure device required to activate the automatic release member is no greater than about 1 lb.

9. A tissue puncture closure device according to claim 1, wherein the automatic driving mechanism further includes at least first and second automatic release members operable upon withdrawal of the closure device from the internal tissue wall puncture, the first automatic release member operable to release the biasing member to distally advance the compaction member, and the second automatic release member operable to release the first slide to move between first and second positions relative to the housing.

10. A tissue puncture closure device according to claim 1, wherein an amount of force applied by the biasing member to the compaction member to compact the sealing pad is no greater than about 1 lb.

11. A tissue puncture closure device for partial insertion into and sealing of a tissue puncture in an internal tissue wall, comprising:
  (a) an anchor configured for positioning on a distal side of the internal tissue wall;
  (b) a sealing pad configured for positioning on a proximal side of the internal tissue wall;
  (c) a filament connected at a distal end to the anchor and sealing pad for slidably cinching the anchor and sealing pad together about the tissue puncture, the sealing pad being slidably disposed on the filament proximal to the anchor;
  (d) a compaction member disposed on the filament;
  (e) a housing arranged proximal of the anchor and sealing pad;
  (f) a storage spool positioned in the housing onto which a proximal end of the filament is wound;
  (g) a biasing member positioned in the housing and automatically activated to drive the compaction member along the filament distally towards the sealing pad upon withdrawal of the tissue puncture closure device;
  (h) a first slide member positioned in and movable relative to the housing, at least the storage spool and biasing member being carried by the first slide member.

12. The tissue puncture closure device according to claim 11, wherein the biasing member is aligned parallel with a direction of movement of the compaction member toward the sealing pad.

13. The tissue puncture closure device according to claim 11, wherein the biasing member is an elongate compression spring.

14. The tissue puncture closure device according to claim 11, further comprising a second slide member positioned in and movable relative to the housing, the second slide member carrying the first slide member and being movable relative to the first slide member.

15. The tissue puncture closure device according to claim 11, further comprising first and second automatic release members operable upon withdrawal of the closure device from the internal tissue wall puncture, the first automatic release member operable to release the biasing member to advance the compaction member, and the second release member operable to release the first slide member to move between first and second positions relative to the housing.

16. The tissue puncture closure device according to claim 11, wherein the sealing pad has a variable cross-sectional size along a length of the sealing plug.

17. The tissue puncture closure device according to claim 11, wherein the sealing pad has a greater cross-sectional size at a distal end portion thereof than a cross-sectional sized at a proximal end portion thereof prior to being compacted with the compaction member.

* * * * *